United States Patent [19]

Hutson, Jr. et al.

[11] 4,454,369

[45] Jun. 12, 1984

[54] HF ALKYLATION PROCESS

[75] Inventors: Thomas Hutson, Jr.; Paul D. Hann, both of Bartlesville, Okla.

[73] Assignee: Phillips Petroleum Company, Bartlesville, Okla.

[21] Appl. No.: 376,076

[22] Filed: May 7, 1982

[51] Int. Cl.³ .............................................. C07C 2/56
[52] U.S. Cl. ................................................... 585/719
[58] Field of Search ......................................... 585/719

[56] References Cited

U.S. PATENT DOCUMENTS

| | | | |
|---|---|---|---|
| 2,372,338 | 3/1945 | Denisten | 585/719 |
| 2,430,333 | 11/1947 | Hadden | 585/719 |
| 2,984,693 | 5/1961 | Cabbage | 585/719 |
| 3,223,749 | 12/1965 | Van Pool et al. | 585/719 |
| 3,579,603 | 5/1971 | Jones | 585/719 |
| 3,669,483 | 12/1962 | Bauer | 585/719 |
| 3,721,720 | 3/1973 | Chapman et al. | 585/719 |
| 3,993,706 | 11/1976 | Mikulicz et al. | 585/710 |
| 4,144,281 | 3/1979 | Chapman et al. | 585/719 |
| 4,373,110 | 2/1983 | Hutson | 585/719 |

Primary Examiner—W. J. Shine
Assistant Examiner—Cynthia A. Prezlock

[57] ABSTRACT

In an HF alkylation process, ASO is separated from HF acid catalyst in a fractionation zone by heating the fractionation zone with a condensible stream comprising liquid and vaporous components. In the process of condensation, latent heat is evolved which is used to effectuate the separation of ASO and HF acid catalyst and dilution of the separated ASO is achieved with the use of the produced condensate.

6 Claims, 1 Drawing Figure

U.S. Patent  Jun. 12, 1984  4,454,369
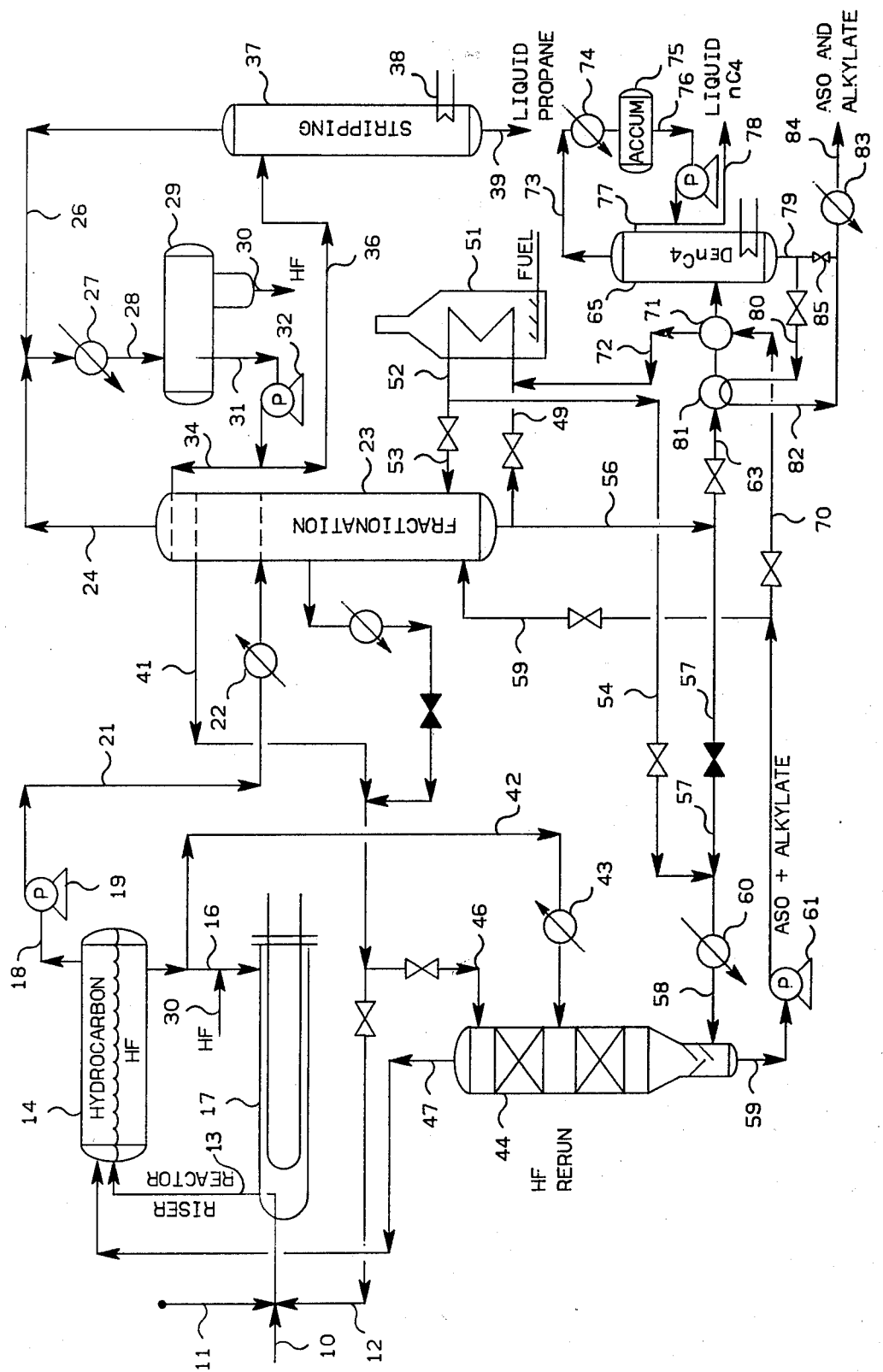

HF ALKYLATION PROCESS

This invention relates to a process for the recovery of a viscous ASO from a HF acid catalyst used in an HF alkylation process.

HF alkylation processes are employed by refining industries to produce high octane blending stocks for gasoline. In such processes, it is inevitable that a portion of the feedstock—usually isobutane—and at least one olefin such as propylene or butene, reacts in a manner to form a hydrocarbon having a higher molecular weight than that of the desired alkylate product. At least a portion of this hydrocarbon comprises acid soluble oils (ASO) which is more soluble in the HF acid catalyst than in hydrocarbon. The resulting ASO has a higher boiling point than the HF acid component. To avoid acid soluble oil build-up in the liquid HF acid alkylation catalyst system it is desirable to periodically or continuously remove same from the HF catalyst so as to be maintained at low levels in liquid HF acid alkylation catalyst system.

It is known from the prior art such as U.S. Pat. No. 3,721,720 that ASO can be removed from hydrogen fluoride (HF) catalyst by removing a slip stream of HF catalyst from the alkylation reaction section and processing this slip stream of HF catalyst in a fractionator under controlled temperature and pressure conditions. The acid soluble oil which is removed as fractionator bottoms is a small stream and contains only a small amount of HF, with ASO being the major component. The ASO stream is recycled to the refinery or passed to a disposal unit.

It is further known to those skilled in the art that a large quantity of material such as heated isobutane vapor which is not condensible in the fractionation zone under operating conditions is required as heating and stripping fluid to separate HF acid catalyst and ASO in a fractionation zone. In addition, once separated the ASO is difficult to remove as a bottoms fraction because it is a very viscous substance. Therefore, a process which renders ASO separation more efficient and easier to handle would be highly desirable.

An object of this invention is to provide an improved process for the removal of viscous ASO from HF acid catalyst present in a fractionation zone. A further object of this invention is to provide an improved process for the handling and removal of ASO from a fractionation zone.

Other aspects, objects, and the several advantages of the present invention will be apparent from a study of this disclosure, the appended claims, and the drawing which shows a schematic flow diagram for carrying out the process of the invention.

In accordance with the present invention wherein, it has been discovered that by passing to a fractionation zone containing ASO dissolved in HF catalyst a heated vapor-containing stream comprising both vaporous and liquid alkylate product and vaporous n-butane wherein the vaporous portions are condensed in the fractionation zone, that a more efficient process for the separation of ASO from HF catalyst is achieved. Condensation of the vaporous portion can be achieved by regulating the temperature and pressure of the fractionation zone to levels where the vaporous portion can no longer exist as such. By condensing the vapor portion of the stream within the fractionation zone, latent heat is released thereby decreasing the amount of heated fluid needed to vaporize the HF to thereby separate ASO therefrom as compared with using a heated vapor such as isobutane which cannot condense in the fractionator under operating conditions. In addition, ASO is rendered less viscous by its being diluted within the fractionation zone with the liquid condensate produced by the condensation of the vapor. Hence, the diluted viscous ASO material is easier to remove from the fractionation zone as a bottoms product.

By the process of the present invention, a higher boiling viscous ASO is separated from a portion of the HF acid catalyst phase in a first fractionation zone by passing to the fractionation zone a heated stream comprising both vaporous and liquid alkylate product and vaporous n-butane, the vaporous portions being condensed in the fractionation zone. The fractionation zone contains ASO dissolved in HF acid catalyst having been or being charged with a stream of ASO dissolved in a lower boiling HF catalyst. The added vaporous stream comprising both liquid and vaporous alkylate and vaporous n-butane is condensed in the fractionation zone, thereby releasing latent heat within the fractionation zone which heat is used to vaporize HF, thereby separating the viscous ASO from the HF. The viscous ASO is at this same time within the fractionation zone diluted with the produced condensate, thereby rendering the ASO easier to be removed from the fractionation zone in a first bottoms fraction comprising alkylate and n-butane.

In a presently preferred embodiment, the first bottoms fraction recovered from the first fractionation zone comprising alkylate and normal butane enriched in ASO which is recovered from the HF catalyst having ASO dissolved therein is charged to a second fractionation zone wherein any remaining HF acid catalyst is removed and a second bottoms fraction comprising ASO, alkylate and n-butane and substantially free in HF acid catalyst is recovered. This HF removal is beneficial because subsequently produced or recovered normal butane is substantially HF-free and can be sold as liquefied petroleum gas (LPG), and the recovered alkylate containing the recovered ASO is free of HF, HF not being wanted in gasoline.

In another preferred embodiment of this invention, the second bottoms fraction, substantially free of HF catalyst and comprising ASO, alkylate, and n-butane is charged to a third fractionation zone wherein normal butane is separated and recovered.

As used herein, the term "isoparaffin" relates to isoparaffin feedstock or recycle to an HF alkylation reactor, to avoid confusion with the product alkylate, which is also technically an isoparaffin.

The term "polymeric material" is intended to include "acid soluble oils" as well as possible products resulting from the contact of the ASO with elevated temperatures below that at which cracking commences.

The accompanying diagrammatic flow sheet illustrates the inventive HF alkylation process.

As shown in the drawing, liquid isobutene feed (10), olefin feed (11) comprising butylenes and some propylene, and liquid recycle isobutane (12) are contacted with liquid HF catalyst from cooler (17) in HF alkylation reactor (13) wherein the isobutane is alkylated with the olefin feed to produce alkylate (isopentane and higher boiling isoparaffinic hydrocarbons). The mass leaving reactor 13 is passed to phase separator 14 wherein a lower liquid HF phase and an upper hydrocarbon phase are formed. The liquid HF is passed via conduit (16) to cooler (17) and back to reactor (13).

Hydrocarbon liquid comprising propane, isobutane, normal butane, and alkylate (isopentane plus) and dissolved HF, is charged via pump (19), conduit (21), and feed preheater (22) to fractionation column (23). Overhead vapor (24), from column (23), comprises propane and HF and is condensed in indirect heat exchanger (27) and passed via conduit (28) to accumulator (29). The separated liquid HF phase is passed via (30) back to the alkylation zone. The liquid hydrocarbon phase (31) is pumped (32) in part as column reflux (34) and a yield portion (36) which is charged to stripper (37), reboiled at (38). Liquid propane is recovered from stripper (37) via conduit (39). Overhead vapor from stripper (37) is passed via conduit (26) and via condenser (27) and conduit (28) to the overhead accumulator (29). (This overhead vapor (26) comprises HF and propane.)

Liquid isobutane (41) is removed from column (23) and is passed, in part, via conduit (12) as the above-referred-to recycle isobutane. A portion of the liquid isobutane is passed via conduit (46) as reflux for HF rerun column (44).

Optionally or along with liquid isobutane removal at (41), a vaporous isobutane stream can be removed from column (23), being removed at a locus below feed (21), as part of the recycle isobutane, after being condensed.

A slip stream of system liquid HF catalyst is passed via conduit (42) and indirect heater (43) to the HF rerun column (44). This stream comprises HF, isobutane, and acid soluble oils (ASO) (polymeric material), and this ASO must be removed from the HF catalyst so that too high of a level of ASO will not be in the system catalyst, so that optimum alkylation will be effected.

From the HF rerun column (44), vaporized HF and vaporized isobutane are removed and passed via conduit (47) to the alkylation zone.

Referring again to column (23), a bottoms liquid stream comprising normal butene, alkylate (isopentane plus) and acid soluble oil (ASO) is, in part, passed via conduit (49) to reboiler (51) and a vapor-liquid mass is passed in part via conduit (53) to reboil column (23) and is passed in part via conduit (54) and conduit (58) as reboil fluid for HF rerun column (44), and to dilute the ASO so that it is easily pumped at (61). Liquid bottoms also is removed via conduit (56) and a portion can be passed via conduit (57) and conduit (58) to HF rerun column (44). A cooler (60) can be used to temper this reboil fluid (58) charged to HF rerun (44). A yield portion of bottoms from column (23) is passed via conduit (63), described further hereinbelow.

Conduit (59) passes the bottoms from HF rerun (44) which stream is pumped (61) to the bottom zone of column (23). Stream (59) comprises ASO, normal butane, alkylate (isopentane and heavier) and can contain some undesired HF therein.

At least a portion of stream (59) is passed via conduit (70) and via indirect heat exchanger (71) and conduit (72) to the reboiler (51). This flow allows use of heat in stream (70) for preheating stream (63), and the recycling of bottoms back through the reboiler (51) to break out HF from organic fluorides which normally are in this bottoms stream.

Stream (63), comprising normal butane, alkylate (isopentanes and heavier isomeric hydrocarbons), and ASO (recovered from the HF rerun column) is preheated in indirect exchanger (81), described herein below, and further preheated in indirect exchanger (71) and the mass is charged to debutanizing column (65). Overhead vapor, comprising normal butane, passes via conduit (73), indirect heat exchanger condenser (74) and to accumulator (75). A portion of the liquid is passed via conduits (76) and (77) as reflux, and the yield normal butane is recovered at (78).

Bottoms (79) from debutanizer (65) comprises alkylate (isopentanes and heavier isoparaffinic hydrocarbons) and the acid soluble oil yield. A portion of stream (79) is passed via conduit (80) and indirect heat exchanger (81), to preheat the feed (63), and via conduit (82), indirect cooler (83) and as product (84) for gasoline blending. As required, a portion of bottoms (79) can by-pass exchanger (81) via conduit (85).

The following calculated example further illustrates the present invention.

EXAMPLE

| Unit Operating Conditions | | |
|---|---|---|
| (13) Reactor: | | |
| Pressure, PSIA, | | 126 |
| Temperature, °F. | | 129 |
| $IC_4$/Olefin Mol Ratio, | | 13 |
| HF/H/C Vol. Ratio, | | 4 |
| Residence Time, sec., | | 30 |
| (23) Fractionator: | | |
| Pressure, PSIA, | | 245 |
| Temperature, °F., | | |
| Top, | | 164 |
| Bottom, | | 400 |
| (44) HF Rerun: | | |
| Pressure, PSIA, | | 150 |
| Temperatures, °F., | | |
| Top, | | 288 |
| Bottom, | | 300 |
| (37) Stripper: | | |
| Pressure, PSIA, | | 330 |
| Temperatures, °F., | | |
| Top, | | 135 |
| Bottom, | | 147 |
| Charge Materials and Yields: | | BBL/DAY |
| (10) Isobutane Feed, | | (a) 3048 |
| (11) Olefin Feed, | | (a) 7637 |
| (12) Recycle Isobutane, | | (a) 60292 |
| (a) Contains some propane and/or normal butane | | |
| (42) HF Catalyst To Rerun | | 699 |
| Wt. % HF | 90 | |
| Wt. % ASO | 3 | |
| Wt. % $H_2O$ | 1 | |
| Wt. % H/C | 6 | |
| (58) Reboil Fluid (Measured as Liquid) | | 839 |
| (59) Total From Tower (44), Bottoms | | 853 |
| Vol. % ASO | | 1.8 |
| (39) Propane Yield, | | 126 |
| Vol. % Propane | 98.7 | |
| (56) Bottoms Yield, | | 8965 |
| Vol. % $nC_4$ | 8.99 | |
| Vol. % ASO | 0.16 | |
| Vol. % $iC_5$ plus | 90.85 | |
| Vol. % Free HF | 0 | |
| (84) Product Yield, | | 8204 |
| Vol. % $nC_4$ | 0.55 | |
| Vol. % ASO | 0.17 | |
| Vol. % $iC_5$ plus | 99.28 | |
| Vol. % Free HF | 0 | |

Reasonable variation and modifications are possible in the scope of the foregoing disclosure without departing from the spirit thereof.

We claim:

1. In an HF alkylation process wherein ASO is removed from an HF acid catalyst in a fractionation zone, the improvement which comprises:

(a) charging a condensible stream comprising vaporous and liquid alkylate and vaporous n-butane to said fractionation zone;

(b) condensing said stream within said fractionation zone thereby producing a condensate (i) which releases heat to effectuate at least partial separation of said HF acid catalyst and ASO in said fractionation zone and (ii) which dilutes the separated ASO to effectuate its removal from said fractionation zone in a bottoms fraction comprising alkylate, n-butane, ASO, and any remaining HF acid.

2. A process as in claim 1 wherein said bottoms fraction is passed to a second fractionation zone wherein HF acid is further separated to produce a substantially HF acid free second bottoms fraction comprising ASO, alkylate, and n-butane.

3. A process as in claim 2 further comprising charging said second bottoms fraction to a third fractionation zone wherein n-butane is separated and a third bottoms fraction comprising alkylate and ASO is recovered as a product.

4. A process for the removal of ASO from HF acid catalyst in an HF alkylation process comprising:

(a) charging a first fractionation zone with a first stream comprising ASO dissolved in HF acid catalyst;

(b) charging said first fractionation zone with condensible second stream comprising vaporous and liquid alkylate and vaporous n-butane;

(c) condensing said second stream in said first fractionation zone to produce (i) heat used to effectuate at least partial separation of ASO and HF acid catalyst and (ii) a condensate which dilutes the separated ASO in said fractionation zone to effectuate its removal from said first fractionation zone in a first bottoms fraction comprising ASO, alkylate, N-butane, and any remaining HF acid.

5. A process as in claim 4 wherein said first bottoms fraction is passed to a second fractionation zone wherein HF acid is further separated to produce a substantially HF acid free second bottoms fraction comprising ASO, alkylate, and n-butane.

6. A process as in claim 5 further comprising charging said second bottoms fraction to a third fractionation zone wherein n-butane is separated and a third bottoms fraction comprising alkylate and ASO is recovered as a product.

* * * * *